United States Patent
Kohayakawa

[11] Patent Number: 5,467,151
[45] Date of Patent: Nov. 14, 1995

[54] EYE REFRACTOMETER HAVING VARIABLE WAVELENGTH ILLUMINATION MEANS

[75] Inventor: Yoshimi Kohayakawa, Yokohama, Japan

[73] Assignee: Canon Kabushiki Kaisha, Tokyo, Japan

[21] Appl. No.: 37,429

[22] Filed: Mar. 26, 1993

[30] Foreign Application Priority Data

Mar. 27, 1992 [JP] Japan .................................. 4-100269
Mar. 12, 1993 [JP] Japan .................................. 5-078883

[51] Int. Cl.⁶ .................................................. A61B 3/103
[52] U.S. Cl. ........................................ 351/213; 351/221
[58] Field of Search .................................. 351/205, 211, 351/213, 221

[56] References Cited

U.S. PATENT DOCUMENTS 3,572,909  3/1971  VanPatten et al. ................ 351/211
3,819,256  6/1974  Bellows et al. .................... 351/211
3,879,113  4/1975  Howland et al. .................. 351/206
4,306,778  12/1981 Wada et al. .................... 351/221 X
4,702,596  10/1987 Nohda ............................ 351/211 X
4,755,041  7/1988  Ishikawa ........................... 351/211
4,938,584  7/1990  Suematsu et al. ................. 351/211

Primary Examiner—William L. Sikes
Assistant Examiner—David R. Parsons
Attorney, Agent, or Firm—Fitzpatrick, Cella, Harper & Scinto

[57] ABSTRACT

An eye refractometer has an illumination system for irradiating a fundus of an examined eye with measurement light, and a light receiving system for receiving a light beam from the fundus of the examined eye irradiated with the measurement light. The illumination system can change the measurement light between visible light and infrared light, and can emit the visible light in a flashing manner. Eye refraction information of the examined eye is detected on the basis of light reception through the light receiving system, and the difference between detection values of the eye refraction information before and after a change of the measurement light.

12 Claims, 3 Drawing Sheets

EYE REFRACTOMETER HAVING VARIABLE WAVELENGTH ILLUMINATION MEANS

BACKGROUND OF THE INVENTION

1. Field of the Invention

This invention relates to an eye refractometer for use in ophthalmic hospitals and optometric offices.

2. Related Background Art

Conventionally, subjective refraction measurement of the eye is performed using visible light. On the other hand, as to autorefractometers, infrared light is widely used. In the case of using infrared light, since chromatic aberrations and the fundus reflection position are different from those in the case of visible light, measured results are compensated for by using average values. However, the occurrence of errors caused by the wavelength difference for each eye examination cannot be avoided.

SUMMARY OF THE INVENTION

A first object of the present invention is to provide an automatic eye refractometer capable of performing accurate measurement.

A second object of the present invention is to provide an eye refractometer capable of performing measurement under natural condition with visible light.

To achieve these objectives, according to the present invention there is provided an eye refractometer comprising an illumination system for irradiating an eye fundus of an examined eye with measurement light, the illumination system being capable of changing the wavelength of the measurement light, and a light receiving system for receiving a light beam from the examined eye fundus irradiated with the measurement light by the illumination system. Eye refraction information of the examined eye is detected on the basis of light reception through the light receiving system, and the difference between detection values of the eye refraction infomation before and after a change of the wavelength of the measurement light is obtained by the light receiving system.

These and other objects and features of the present invention will become apparent from the following detailed description of embodiments of the invention.

DETAILED DESCRIPTION OF THE PREFERRED EMBODIMENTS

Figure 1:
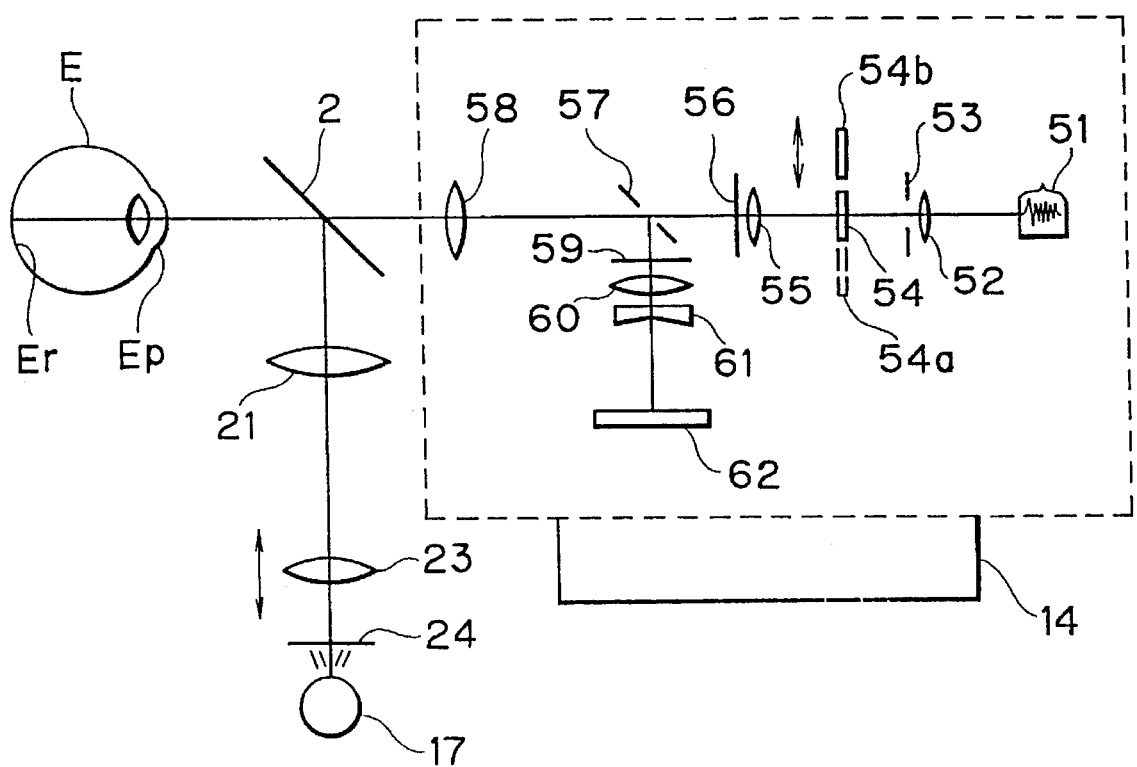
FIG. 1 is a schematic diagram of the construction of a first embodiment of the present invention.

FIG. 1 is a diagram of the construction of a first embodiment of the present invention. A halogen lamp 51 capable of emitting a light beam for an instant is provided as a measurement light source. A lens 52, a central aperture stop 53 conjugage with an emmetropic fundus of an eye E to be examined, an interchangeable filter 54, a lens 55, a central aperture stop 56 conjugate with a pupil Fp of the eye E, a mirror 57 with an aperture, a lens 58, and a half mirror 2 are disposed in an optical path from the halogen lamp 51 to the eye E. A peripheral 6-hole stop 59 conjugate with the pupil, a lens 60, a separation prism 61 formed of six wedge prisms, and a two-dimensional light position sensor 62 formed of a charge coupled device (CCD) and conjugate with the emmetropic fundus are arranged in the direction of reflection from the aperture mirror 57. A lens 21, a moving lens 23, a fixed visual mark 24, and a visual mark light source 17 are arranged in the direction of incident upon the half mirror 2. The filter 54 is separately formed of a filter 54a which transmits infrared light while cutting visible light, and a filter 54b which transmits visible light while cutting infrared light. These filters 54a and 54b can be replaced with each other in the optical path. A driving system for driving a refractometer body is indicated at 14.

In this arrangement, the light beam from the halogen lamp 51 passes through the lens 52, the central aperture stop 53, the filter 54a, the lens 55, the central aperture stop 56, the aperture mirror 57, the lens 58 and the half mirror 2 to project a spot of infrared light to a fundus Er of the examined eye E. A beam of light reflected by the fundus Er is returned through the same optical path, is reflected by the aperture mirror 57, passes through the peripheral 6-hole stop 59, the lens 60 and the separation prism 61, and is received as six reflected light beams by the two-dimensional light position sensor 62. The positions on this sensor 62 at which the six reflected light beams are received correspond to eye refracting powers along different meridional lines on the examined eye, and refraction values with respect to the meridional lines are calculated from the received positions.

On the other hand, a light beam from the visual mark light source 17 illuminates the fixed visual mark 24, and light of an image of the visual mark travels through the moving lens 23 and the lens 21 and is reflected by the half mirror 2 to be projected to the examined eye E. At this time, until the examined eye E is induced to set a far point diopter by moving the lens 23, eye refraction values are measured by using infrared light through the filter 54a. Thereafter, the filter 54a is replaced with the filter 54b and eye refraction values are measured by using visible light. In this case, a visible measurement light beam is projected for an instant, and an after image disappears soon so that the examined eye E is maintained in a natural condition. Since visible light is used as the measurement light beam, there is no need for the compensation such as that described above with respect to the conventional art.

Figure 2:
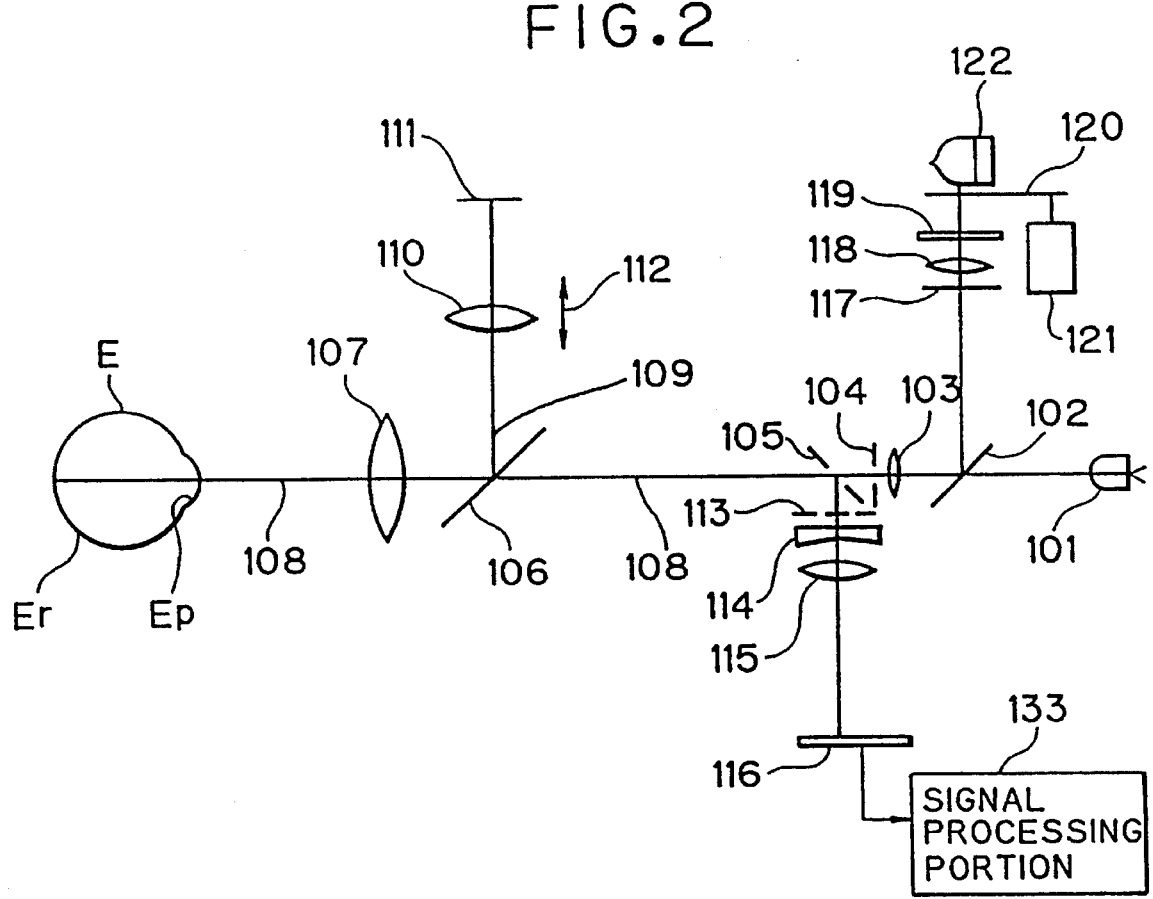
FIG. 2 is a schematic diagram of the construction of a second embodiment of the present invention.

FIG. 2 is a diagram of the construction of a second embodiment of the present invention. As illustrated, the eye refractometer of this embodiment has a light emitting diode (LED) provided as a near infrared light source, a dichroic mirror 102 which transmits near infrared light but reflects visible light, a lens 103, a central aperture stop 104 conjugate with an emmetropic fundus of an eye to be examined, an aperture mirror 105 having an aperture in an optical axis, a mirror 106 which partially transmits and reflects visible light and transmits near infrared light, an objective lens 107, a fixed visual mark projection lens 110, a fixed visual mark 111, a 6-hole stop 113 having six holes around an optical axis and conjugate with a pupil Ep of the examined eye, a separation prism 114 formed of six wedge prisms, a lens 115, a CCD area sensor 116 for receiving six light beams formed by the 6-hole stop 113, a central aperture stop 117 having an aperture of the same shape as the light source 101, a lens 118, a filter 119 having a spectral transmissivity similar to the visual sensitivity, a shutter 120, a motor 121 for driving the shutter 120 to open or close the same, a lamp 122 provided as a visual light source 122, and a signal processor 133.

The fixed visual mark 111 is projected to the examined eye E along an optical axis 109 through the lenses 110 and 107 and the mirror 106. At the time of eye refraction measurement, the lens 110 is moved in the direction of the arrows to change the eye diopter while the fixed visual mark 111 is viewed with the examined eye E.

When an eye refraction measurement is performed by using a near infrared light beam as a measurement light beam, the near infrared light beam from the LED 101 travels along an optical axis 108 through the dichroic mirror 102, the lens 103, the central aperture stop 104, the aperture mirror 105, the mirror 106 and the objective lens 107 and is projected from a center of the pupil Ep of the examined eye E to a fundus Er as a spot of light. Light reflected by the fundus is returned through the same optical path along the optical axis 108 and is reflected by the aperture mirror 105 to be incident upon the 6-hole stop 113. Light emerging from the 6-hole stop 113 passes through the separation prism 114 and the lens 115 to be received as six light beams on a light receiving surface of the CCD area sensor 116. An output signal from the CCD area sensor 116 is converted from an analog form to a digital form in the signal processor 133 and is stored as data in an internal memory. From the stored data including information on the incident positions of the six beams on the light receiving surface, refraction values of the examined eye are calculated by an internal operational section of the signal processor 133. A well-known method is used to calculate eye refraction values from the incident position of the six beams in accordance with this embodiment, and it will not be explained in this specification.

When an eye refraction measurement is performed by using a visible light beam as a measurement light beam, the shutter 120 is opened for an instant by the motor 121. Then, a visible light beam from the lamp 122 travels via the filter 119, the lens 118, the central aperture stop 117 and dichroic mirror 102 and travels along the optical axis 108 through the same optical path as that for the infrared light to be projected as a spot of light to the fundus Er. Reflected light from the fundus Er travels through the same optical path as that for the infrared light to be received as six light beams on the light receiving surface of the CCD area sensor 116. An output signal therefrom is processed in the same manner as in the case of the infrared light.

The refraction values of the visible light and the infrared light is successively measured. The internal memory of the signal processor 133 has a memory capacity for two groups of image data to successively store both groups of incidence data of the six light beams on the light receiving surface obtained by the visible light irradiation and the near infrared light irradiation. Thereafter, the difference between the 6-beam incidence positions of the two measurement beams (or the difference between the eye refraction values. calculated on the basis of the 6-beams incidence positions) is obtained by the calculation section of the signal processor 133, and is stored as calibration data. Subsequent measurements are performed by using only near infrared light, and the results of the measurements are calibrated by using the stored calibration data and are thereafter outputted by an unillustrated output means. It is thereby possible to obtain eye refraction values as accurate as those obtained by the visible light.

If the increase in illuminance of the lamp 122, when the lamp is turned on, is sufficiently fast, and if the measurement light can be received before pupil contraction or a blink occurs, the shutter 120 may be removed and instantaneous illumination may be effected by the driving of the lamp 122. A stroboscopic device may be used instead of the lamp 122. In such a case, there is no need for the shutter 120.

Figure 3:
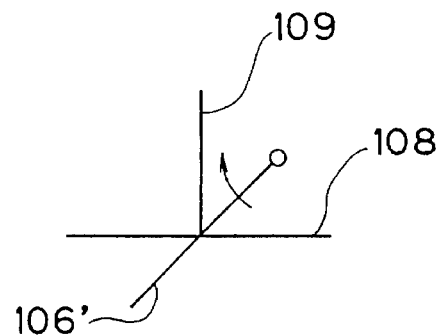
FIG. 3 is a schematic diagram of the construction of a portion of the second embodiment.

As shown in FIG. 3, the mirror 106 may be replaced with a quick return mirror 106'. At the time of diopter induction, the quick return mirror 106' is at the position indicated in FIG. 3, and is swingingly moved upward in the direction of the arrow at the time of eye refraction measurement.

Figure 4:
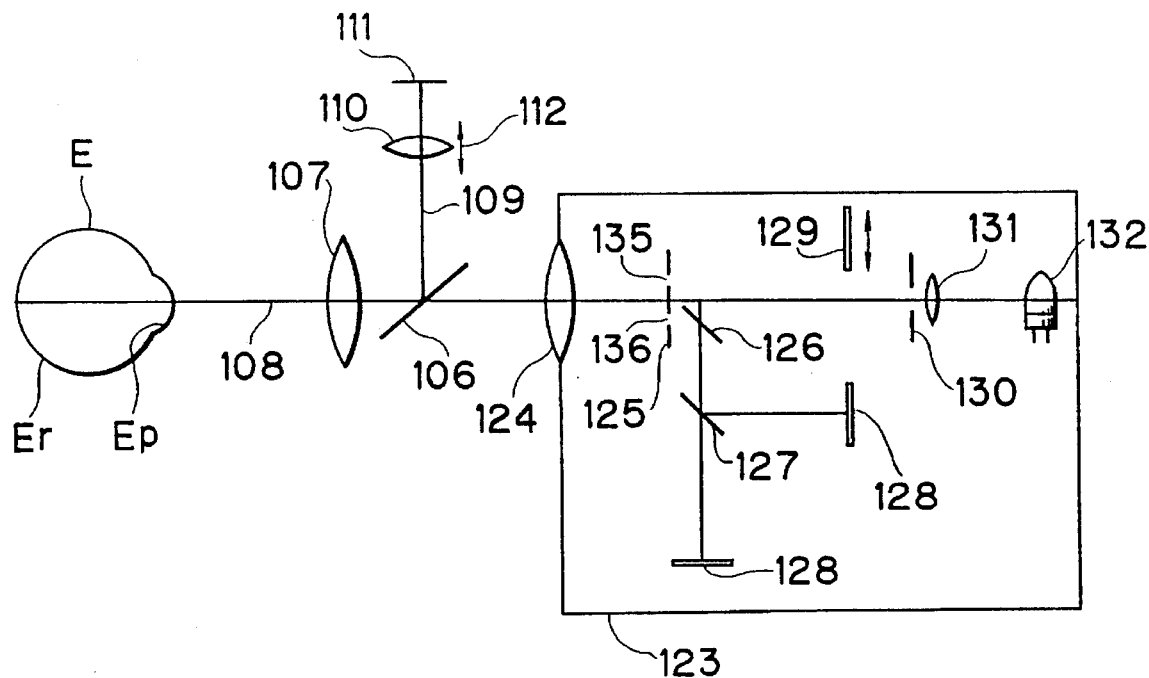
FIG. 4 is a schematic diagram of the construction of a third embodiment of the present invention.
Figure 5:
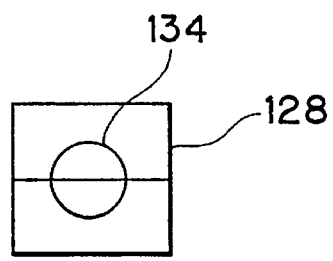
FIG. 5 is a schematic diagram of a sensor surface.

FIG. 4 is a diagram of a third embodiment of the present invention. Components corresponding or identical to those of the second embodiment are indicated by the same reference characters. The eye refractometer shown in FIG. 4 has a unit 123 capable of moving in an optical axis 108 and capable of rotating about the optical axis 108. The unit 123 includes the following members: a lens 124, a stop 125 having two apertures 135 and 136 and conjugate with pupil Ep, a mirror 126 disposed in a position such as to deviate from the optical axis 108, a dichroic mirror 127 for separating visible light and infrared light, sensors 128, a visible light cutting filter 129, a central aperture stop 130, a lens 131, and a lamp 132 positioned such as to be conjugate with the aperture stop 130. Each of the sensors 128 is constituted of two adjacent photoelectric surfaces, as shown in FIG. 5.

A fixed visual mark projection system of this embodiment functions in the same manner as that of the second embodiment.

When eye refraction measurement is performed by using an infrared light beam as a measurement light beam, the filter 129 is inserted across the optical axis 108, the near infrared light beams from the lamp 132 travels along the optical path 108 through the lens 131, the central aperture stop 130, the filter 129, the aperture 135 of the stop 125, the mirror 106 and the objective lens 107 to be projected from the center of the pupil Ep of the examined eye E to the fundus Er as a spot of light. Reflected light from the fundus travels the optical path in the opposite direction, passes through the aperture 136 of the stop 125, is reflected by the mirror 126, and reaches one of the sensors 128 via the dichroic mirror 127. The position of the light beam on the sensor varies according to the eye refracting power along a predetermined meridional line on the examined eye. Therefore, the unit 123 is moved along the optical axis 108 so that the incident light beam is equally distributed on the two photoelectric surfaces of the sensor, as shown in FIG. 5, by monitoring outputs from the two photoelectric surfaces. Since the light beam is formed as a parallel light beam between the lenses 107 and 124, the conjugate relationship of the optical system can be maintained even when the unit 123 is moved along the optical axis 108. The position of the unit 123 at this time corresponds to the eye refracting power along the predetermined meridional line on the examined eye. Therefore, eye refraction values along the predetermined meridional line on the examined eye can be measured by an unillustrated calculation-means on the basis of the relationship between the unit position and the eye refracting power.

To perform eye refraction measurement with respect to another meridional line on the examined eye, the unit 123 is rotated on the optical axis 108 to a position corresponding to the meridional line along which the refracting power is to be measured, and the measurement is performed in the same manner as in the above.

When eye refraction measurement is performed by using a visible light beam as a measurement light beam, the filter is removed and the lamp 132 is lighted so as to effect flash illumination, and the measurement is performed in the same manner as the near infrared light measurement with the sensor 128 different from the one used at the time of the infrared light measurement.

Calibration data is formed from the difference between the thus-obtained measurement results in the same manner as the second embodiment. Subsequent measurements are performed by using the infrared light beam as a measurement light beam, while the filter 129 is maintained in the inserted state. After being calibrated with the calibration data, measurement results are outputted to an illustrated output unit.

It is desirable that the positions of the sensors 128 on the optical axis are previously shifted according to the difference between the fundus conjugate positions with respect to the detected light beams so that the fundus conjugate relationship is established at generally the same positions with respect to visible and near infrared light.

The calibration may be performed with respect to a meridional direction alone. In such a case, there is no need for unit rotation.

Since the examined eye is instantaneously irradiated with visible light at the time of visible light measurement, there is no risk of the examined eye being excessively dazzled so that subjective refraction test or the like to be followed is seriously influenced. By the effect of calibration, the accuracy of measurement using infrared light can be as high as the accuracy of visible light measurement.

What is claimed is:

1. An eye refractometer comprising:

an illumination system for irradiating a fundus of an eye to be examined with measurement light, said illumination system comprising means for changing the wavelength of the measurement light;

a photodetecting system for receiving a light beam from the fundus of the eye to be examined irradiated with the measurement light by said illumination system; and signal processing means for detecting eye refraction information of the eye to be examined on the basis of output signals from said photodetecting system receiving the light beam when said illumination system irradiates the fundus of the eye to be examined with the measurement light of different wavelengths.

2. An eye refractometer according to claim 1, wherein said illumination system and said photodetecting system use a common objective portion.

3. An eye refractometer according to claim 1, further comprising a mark projection system for presenting a mark to the examined eye, said mark projection system projecting the mark from an illumination optical path of said illumination system through a light splitting member.

4. An eye refractometer according to claim 1, wherein, in said illumination system, said changing means comprises an interchangeable filter in an optical system which is interchanged to change the wavelength of the measurement light.

5. An eye refractometer according to claim 1, wherein said illumination system includes light sources for emitting light of different wavelengths to be changed, and an optical path combining member for leading the light from each light source to the fundus of an eye to be examined through the same optical path.

6. An eye refractometer according to claim 1, wherein said illumination system changes the wavelength of the measurement light from light not visible to the eye to visible light, and the visible light is emitted for an instant.

7. An eye refractometer according to claim 1, wherein eye refraction information of the eye to be examined along a plurality of meridional directions is detected substantially simultaneously by the light reception through said photodetecting system.

8. An eye refractometer comprising:

an illumination system for irradiating a fundus of an eye to be examined with measurement light, said illumination system comprising means for changing the wavelength of the measurement light;

a photodetecting system for receiving a light beam from the fundus of the eye to be examined irradiated with the measurement light by said illumination system; and signal processing means for detecting eye refraction information of the eye to be examined on the basis of output signals from said photodetecting system receiving the light beam, when said illumination system irradiates the fundus of the eye to be examined with the measurement light of different wavelengths, wherein said changing means changes the measurement light to visible light and near infrared light.

9. An eye refractometer comprising:

an illumination system for irradiating a fundus of an eye to be examined with measurement light, said illumination system comprising means for changing the wavelength of the measurement light;

a photodetecting system for receiving a light beam from the fundus of the eye to be examined irradiated with the measurement light by said illumination system; and signal processing means for detecting eye refraction information of the eye to be examined on the basis of the output signal from said photodetecting system receiving the light beam, wherein said photodetecting system includes a rotatable portion to detect the eye refraction information of the examined eye along a plurality of directions.

10. An eye refractometer comprising:

an illumination system for irradiating a fundus of an eye to be examined with measurement light, said illumination system comprising means for changing the wavelength of the measurement light;

a photodetecting system for receiving a light beam from the fundus of the eye to be examined irradiated with the measurement light by said illumination system;

signal processing means for detecting eye refraction information of the eye to be examined on the basis of the output signal from said photodetecting system receiving the light beam; and a mark projection system for presenting a mark to the eye to be examined, said mark projection system projecting the mark from an illumination optical path of said illumination system by means of a quick return mirror.

11. An eye refractometer comprising:

an illumination system for irradiating a fundus of an eye to be examined with measurement light and said illumination system emitting visible light as the measurement light so that the fundus of the eye to be examined is illuminated with flash light;

a photodetecting system for receiving a light beam from the fundus of the eye to be examined irradiated with the measurement light by said illumination system; and signal processing means for detecting eye refraction information of the eye to be examined on the basis of the output signal from said photodetecting system receiving the light beam.

12. An eye refractometer comprising:

an illumination system for illuminating a fundus of an eye to be examined at least at two different wavelengths;

a photodetecting system for receiving a light beam from the fundus of the eye to be examined illuminated with light from said illumination system; and signal processing means for detecting eye refraction information of the eye to be examined at each of the two different wavelengths on the basis of the output signal from said photodetecting system receiving the light beam.

* * * * *

UNITED STATES PATENT AND TRADEMARK OFFICE
CERTIFICATE OF CORRECTION

PATENT NO. : 5,467,151
DATED : November 14, 1995
INVENTOR(S) : YOSHIMI KOHAYAKAWA It is certified that error appears in the above-indentified patent and that said Letters Patent is hereby corrected as shown below:

<u>Column 1,</u>
    line 40, "infomation" should read --information--;
and
    line 67, "conjugage" should read --conjugate--.

<u>Column 3,</u>
    line 56, "values." should read --values--.

<u>Column 4,</u>
    line 57, "calculation-means" should read
--calculation means--.

Signed and Sealed this

Ninth Day of April, 1996

*Attest:*

BRUCE LEHMAN

*Attesting Officer*     *Commissioner of Patents and Trademarks*